US00PP11061P

United States Patent [19]

Chamberlin, Sr.

[11] Patent Number: Plant 11,061

[45] Date of Patent: Sep. 14, 1999

[54] PLUM TREE NAMED 'YELLOW #503'

[75] Inventor: Thomas O. Chamberlin, Sr., Visalia, Calif.

[73] Assignee: Corrin Family Trust, Reedly, Calif.

[21] Appl. No.: 08/985,022

[22] Filed: Dec. 4, 1997

[51] Int. Cl.[6] ..... A01H 5/00

[52] U.S. Cl. ..... Plt./184

[58] Field of Search ..... Plt./38.1, 184

*Primary Examiner*—Howard J. Locker
*Assistant Examiner*—Anne Marie Grünberg
*Attorney, Agent, or Firm*—Richard A. Ryan

[57] ABSTRACT

A new and distinct variety of plum tree which is distinguished by producing fruit which are mature for harvesting and shipment approximately June 16 to June 20 in the San Joaquin Valley of central California and wherein the fruit is small and round with a crisp and firm flesh which does not bruise easily and having a bright yellow-green skin coloration.

1 Drawing Sheet

BACKGROUND OF THE NEW VARIETY

The present invention relates to a new and distinct variety of plum tree, which will hereinafter be denominated varietally as the 'Yellow #503' plum tree, and, more particularly, to such a plum tree which produces very small bright yellow-green fruit which are mature for commercial harvesting and shipment approximately June 16 to June 20 in the San Joaquin Valley of central California.

The commercial market for tree fruit, as with other fresh fruit and vegetables, is changing to reflect consumer desire for packaged products. As the fruit market develops to reflect consumer desires, the shipping and handling characteristics of fruit that can be included in packaged products become significantly more important. In order for fruit to be suitable to satisfy the market demand for packaged products, it should be of a smaller than usual size, have superior flavor and visual characteristics and be of a firm nature suitable for packaging in plastic bags and other containers.

ORIGIN AND ASEXUAL REPRODUCTION OF THE NEW VARIETY

The plum tree of the present invention was discovered by the inventor as a chance seedling in a nursery located near Reedley in the San Joaquin Valley of central California. The inventor discovered the seedling from seed planted in the nursery in 1989. The first fruit was seen on this seedling in June, 1992. As the fruit matured, it was examined as to size, shape, coloration, ripening date, flavor, texture and as to other criteria which were sought in a plum variety having the desired commercial potential. The initial fruit was very small with a heavy crop having good flavor. The seedling was marked for further testing.

Graft wood was collected from this seedling in the Winter of 1992–1993. Trees were grafted onto Lovell rootstock in the early Spring of 1993 in the testing part of the nursery. The first fruit from these asexually produced trees of the new variety was observed by the inventor in the summer of 1995 and again in 1996. The crop on these trees of the new variety was very heavy with small yellow-green fruit, which had very good flavor. The inventor did not thin the fruit on these trees as it was desired to obtain small fruit for a new market called Lunch Pack. Fruit for this market is packed in eight ounce or one pound packages. The fruit from this new variety of plum tree had the size and flavor desired for this new market.

The harvest time for the asexually produced trees of this new variety was about mid-June, the same time as the parent seedling. These trees produced the same small, round fruit having flesh of a firm texture. The flavor of the fruit was very good. The skin coloration of the fruit was the same bright yellow-green color and the leaves matched the leaves on the parent seedling. The bark and growth pattern characteristics also matched the parent seedling. The inventor has confirmed that the asexually reproduced trees of the new variety are the same in all respects to the parent seedling.

SUMMARY OF THE NEW VARIETY

The 'Yellow #503' plum tree is characterized by producing a fruit which has a bright yellow-green skin coloration and is ripe for harvesting and shipment approximately June 16 to June 20 in the San Joaquin Valley of central California. The fruit of the new variety are small in size, fully round in shape and possess an excellent flavor. The pit of this fruit is very small, resulting in a lot of good flavored flesh to eat despite the small size of the fruit. The fruit has been determined to have outstanding storage life, retaining its firm flesh of very good flavor even after thirty (30) days in cold storage. These characteristics of this fruit make it particularly suitable for packaging for sale in the Lunch Pack market.

The asexually produced plum tree of the present invention will set a very heavy crop of fruit that is easy to harvest. The crop does not have to be thinned, thereby saving those costs. The manner in which the tree grows makes it easy to place it on a six-foot trellis, as is done with grapes. This method of growing makes it easy to shape the tree and harvest the crop.

BRIEF DESCRIPTION OF THE DRAWING

The drawing is a color photograph showing mature fruit of the new variety including a first in side elevation, a second in bottom plan view showing the apex area thereof, a third in top plan view showing the base thereof, a fourth in side elevation showing the suture thereof, a fifth sectioned and laid open to show the stone in one section and the stone cavity in the other section, and a sixth showing the stone itself; and representative foliage, all of the new variety.

DETAILED DESCRIPTION

Referring more specifically to the pomological details of this new and distinct variety of plum tree, the following has been observed under the ecological conditions prevailing at the orchard of origin, which is located near Reedley, Calif. All major color code designations are by reference to the *Inter-Society Color Council, National Bureau of Standards.* Common color names are also occasionally employed.

TREE

Generally:
- *Size.*—Normal plum tree size but due to the type of growth and fruit setting tree can be grown in different ways.
- *Vigor.*—Vigorous.
- *Chilling requirements.*—250 hundred to 400 hundred hours.
- *Figure.*—Bushy tree to height of eight feet and four feet wide.
- *Productivity.*—Small size plum, typically; formed in clusters on numerous spurs. Average of fifty (50) pounds per tree in year four.
- *Regularity of bearing.*—Will bear a good crop every year.

Trunk:
- *Size.*—Normal diameter.
- *Surface texture.*—Normal plum tree bark with many long vertical splits and small lenticels.
- *Color.*—Light brown bark (58-M.Br).
- *Lenticels — numbers.*—Small lenticels, approximately 25 per square inch.
- *Lenticels — vertical splits.*—5.08 cm (2 inches) to 7.62 cm (3 inches) long and about 0.32 cm (⅛ inch) diameter — color (53 M.O.).

Branches:
- *Size.*—Normal, depending on pruning and shaping.
- *Surface texture.*—Normal. Same characteristics as trunk.
- *Color.*—Light brown (58-M.Br.).
- *Color — One year or older wood.*—Same.
- *Surface texture — Immature growth.*—Smooth.
- *Lenticels — numbers.*—Approxiamtely 25–28 per square inch.
- *Lenticels — size.*—Very small.

LEAVES

Size:
- *Average length.*—6.35 cm (2½ inches) to 6.67 cm (2⅝ inches).
- *Average width.*—3.18 cm (1¼ inches) to 3.49 cm (1⅜ inches).

Form: Lanceolate.

Color:
- *Upwardly disposed surface.*—Dark green (126 d.Ol.G.).
- *Downwardly disposed surface.*—Light green (137 d.Y.G.).

Marginal form:
- *Generally.*—Very finely serrate.

Glandular characteristics: No glands found on stem.

Petiole:
- *Size.*—Normal.
- *Length.*—1.27 cm (½ inch.).
- *Width.*—0.160 cm (1/16 inch).

FLOWERS

Flower buds: Information was taken as white started to show at apex of bud.
- *Length.*—0.48 cm (3/16 inch).
- *Diameter.*—0.32 cm (⅛ inch).
- *Shape.*—Slightly elongated.
- *Other characteristics.*—This fruit sets a very heavy set of buds on fruit spurs, will range in number of buds per spur from about 12 to 23 or 24. Fruit spurs are about 2.54 cm (1 inch) apart on branches.
- *Color.*—Light green (115 V.Y.G.)

Date of bloom: Approximately February 15$^{th}$ to the 24$^{th}$ at Reedley, Calif.

Size:
- *Petal — length.*—0.64 cm (¼ inch).
- *Petal — diameter.*—0.64 cm (¼ inch).
- *Bloom. — diameter.*—2.54 cm (1 inch).

Shape: Each petal very small and round in appearance.

Fragrance: No characteristic fragrance.

Petals:
- *Color*—White (263 White).

Pedicel:
- *Length.*—Ranges from 0.48 cm (3/16 inch) to 0.64 cm (¼ inch), depending on location.

FRUIT

Maturity when described: Ripe for commercial harvesting and shipment approximately June 16$^{th}$ to June 20$^{th}$ near Reedley in the central San Joaquin Valley of California.

Size:
- *Generally.*—Small.
- *Average diameter.*—Approximately 3.49 cm (1⅜ inches) to 3.81 cm (1½ inches).
- *Weight.*—1 to 1½ ounces each.
- *Sugar content.*—20 Brix.

Form:
- *Uniformity.*—Good.
- *Symmetrical.*—Yes. Very round in appearance, with wide base and rounded apex area.

Suture:
- *Generally.*—Smooth, very slightly indented.
- *Length.*—Approximately 2.86 cm (1⅛ inches) to 3.18 cm (1¼ inches).

Vertical surface:
- *Generally.*—Very smooth, slightly rounded to almost flat.

Stem cavity:
- *Generally.*—Rounded.
- *Depth.*—Approximately 0.32 cm (⅛ inch).
- *Base.*—Wide and rounded.
- *Apex.*—Slightly rounded to almost flat.

Pistil point: None

Stem:
- *Generally.*—Normal.
- *Length.*—1.11 cm (7/16 inch).
- *Width.*—0.16 cm (1/16 inch).

Skin:
- *Thickness.*—Very light but firm.
- *Texture.*—Smooth and tenacious to the flesh.
- *Tendency to crack.*—None.
- *Color.*—Bright yellow with green under color. (99S.G.Y.)
- *Pubescence.*—None.

Flesh:
- *Flesh color.*—Yellow (98 brill.G.Y.).
- *Surface of pit cavity.*—Not a free stone. Flesh tight to stone.
- *Juice production.*—Very juicy. Almost no acid taste.
- *Flavor.*—Good — mild and sweet.

*Aroma*—Slight.
*Texture.*—Smooth, juicy and crisp at picking time.
*Fibers.*—Numbers — None.
*Ripening.*—Even.
*Eating quality.*—Very good.

Stone:
*Attachment.*—Cling.
*Fibers.*—Number — None.
*Size — length.*—1.43 cm (9/16 inch).
*Size — width.*—1.11 cm (7/16 inch).
*Size — thickness.*—0.64 cm (1/4 inch).
*Form — Generally.*—Oval in appearance.
*Apex — Shape.*—Very slight point.
*Color.*—Yellow Brown (68 S.OY.).
*Base.*—Very small and round.
*Sides — generally.*—Almost smooth.
*Ridges.*—None.
*Tendency to split.*—None.

Use: Fresh fruit market.

Keeping quality: Very good, has been kept in cold storage for over 30 days.

Resistence to disease: No disease noted to date.

Harvesting: Fruit is very firm at harvest time.

Shipping and handling qualities: Due to firm nature of fruit, it does not bruise easily and should handle and ship very well. Suitable for being packed in 16 oz. (one pound) plastic bags for Lunch Pack market.

Although the new variety of plum tree possesses the described characteristics noted above as a result of the growing conditions prevailing near and in the central part of the San Joaquin Valley of California, it is to be understood that variations in the usual magnitude and characteristics incident to changes in growing conditions, irrigation, fertilization, pruning, pest control, climatic variation and the like are to be expected.

Having thus described an illustrated my vew variety of plum tree, what I claim as new and desire to be secured by Plant Letters Patent is:

1. A new and distinct variety of plum tree substantially as illustrated and described which is distinguished by producing small, fully rounded fruit having a bright yellow-green skin coloration and which are mature for commercial harvesting and shipment approximately June $16^{th}$ to June $20^{th}$ in the San Joaquin Valley of central California.

* * * * *

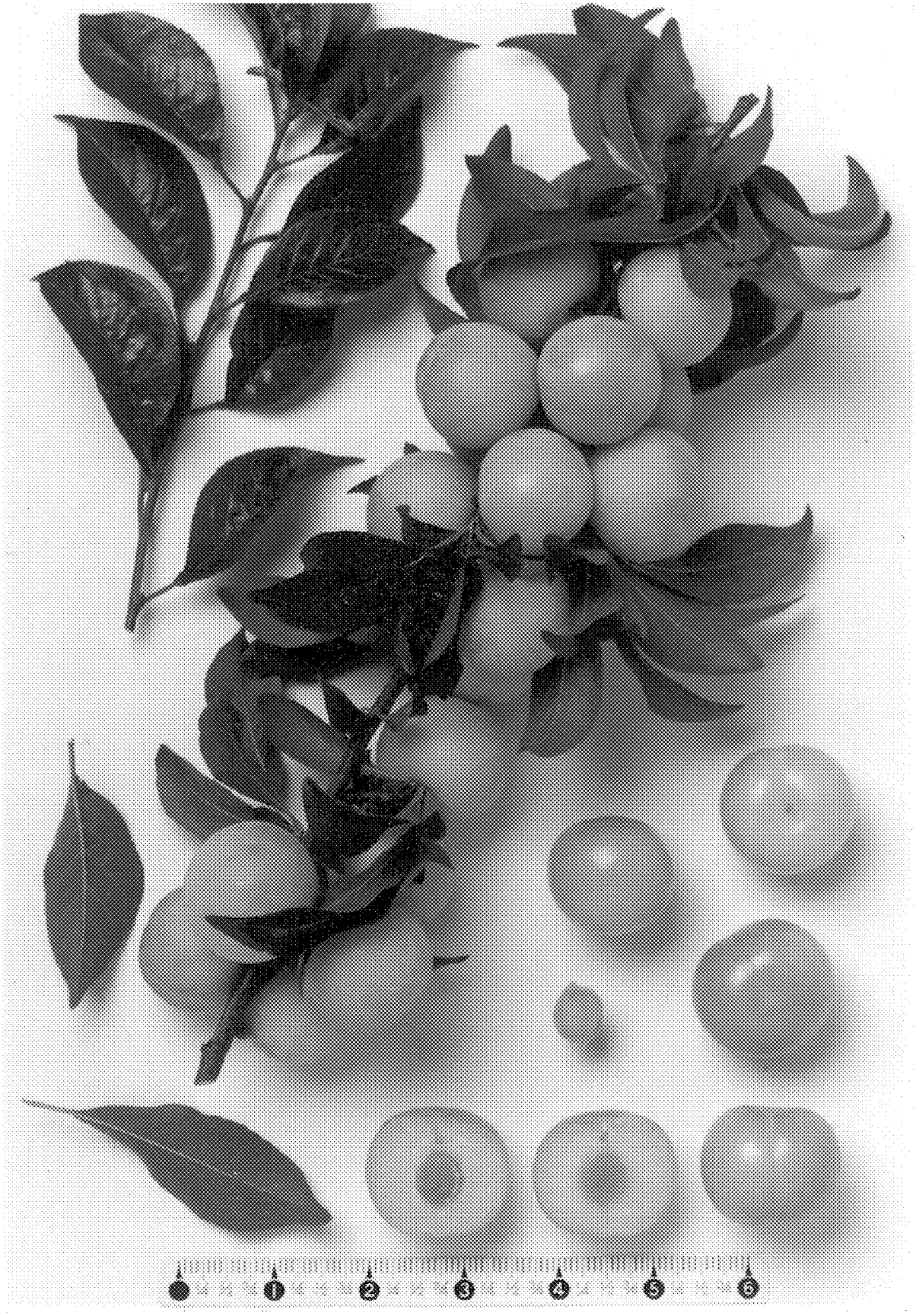
0
1
2
3
4
5
6